(12) United States Patent
Lordo

(10) Patent No.: US 7,672,973 B2
(45) Date of Patent: Mar. 2, 2010

(54) PATIENT INTERFACE DEVICE OR COMPONENT SELECTING SYSTEM AND METHOD

(75) Inventor: Richard J Lordo, Allison Park, PA (US)

(73) Assignee: RIC Investments, LLC, Wilmington, DE (US)

( * ) Notice: Subject to any disclaimer, the term of this patent is extended or adjusted under 35 U.S.C. 154(b) by 1315 days.

(21) Appl. No.: 10/738,512

(22) Filed: Dec. 17, 2003

(65) Prior Publication Data

US 2004/0133604 A1 Jul. 8, 2004

Related U.S. Application Data

(60) Provisional application No. 60/434,459, filed on Dec. 18, 2002.

(51) Int. Cl.
*G06F 17/00* (2006.01)

(52) U.S. Cl. .................... 707/104.1; 707/102; 705/3

(58) Field of Classification Search .............. 707/1, 707/3, 6, 5, 10, 104.1, 102; 128/200.24, 128/200.11, 200.19, 200.21, 201.24, 206.21, 128/206.24; 705/2, 1, 3
See application file for complete search history.

(56) References Cited

U.S. PATENT DOCUMENTS

| | | | |
|---|---|---|---|
| 6,012,034 A * | 1/2000 | Hamparian et al. ............ 705/2 |
| 6,397,847 B1 | 6/2002 | Scarberry et al. |
| 6,611,846 B1* | 8/2003 | Stoodley .................. 707/104.1 |
| 2002/0103505 A1* | 8/2002 | Thompson ..................... 607/1 |
| 2003/0204415 A1* | 10/2003 | Knowlton ...................... 705/2 |
| 2003/0229514 A2* | 12/2003 | Brown ........................... 705/2 |

* cited by examiner

*Primary Examiner*—Greta L Robinson
(74) *Attorney, Agent, or Firm*—Michael W. Haas

(57) ABSTRACT

A patient interface device selection system that includes a database storing a plurality of sets of data. Each set of data in the plurality of sets of data is associated with a unique patient interface device or a component thereof. A patient data collection system, such as a measuring device, acquires a set of patient data that correspond to at least one characteristic of a patient. A processing system compares the acquired patient data with the plurality of sets of data, and determines the patient interface device or the component thereof that is suitable for use by such a patient based on a result of the comparison.

56 Claims, 2 Drawing Sheets

PATIENT INTERFACE DEVICE OR COMPONENT SELECTING SYSTEM AND METHOD

CROSS-REFERENCE TO RELATED APPLICATIONS

This application claims priority under 35 U.S.C. §119(e) from provisional U.S. patent application No. 60/434,459 filed Dec. 18, 2003, the contents of which are incorporated herein by reference.

BACKGROUND OF THE INVENTION

1. Field of the Invention

The present invention pertains to an automated system and method for selecting a patient interface device or a component of a patient interface device from a plurality of known patient interface devices or components for use by a patient based on at least one characteristic of the patient.

2. Description of the Related Art

There are many instances where it is necessary to communicate a flow of gas with an airway of a patient. For example, it is well known to deliver a supply of breathing gas to an airway of a patient to treat a medical disorder, such as sleep apnea syndrome, and, in particular, obstructive sleep apnea (OSA), congestive heart failure, or to ventilate a patient who has a compromised respiratory ability. It is also well known to monitor the condition of a patient by monitoring the gases inspired and/or expired by the patient. Typically, such monitoring involves evaluating the composition, flow rate and/or pressure of the gases over a period of time.

A patient interface device is used to communicate the flow of gas with the patient's airway. For present purposes, this includes any device that accomplishes this function, such as a nasal mask, nasal/oral mask, full face mask that covers the user's entire face, nasal cannula, etc. A typical patient interface device includes a mask, which provides a flexible seal covering the nose, mouth, or both, and a headgear that secures the mask to the user's head.

A requisite of such patient interface devices is that they provide an effective seal against the user's face to prevent leakage of the gas being supplied or received. It is often the case, in prior patient interface configurations, that a good mask-to-face seal is attained only with some discomfort to the user. This problem is most crucial because such patient interface devices are typically worn for an extended period of time, such as overnight while the patient is asleep. One concern in such a situation is that a user may avoid wearing an uncomfortable mask, defeating the purpose of the prescribed pressure support therapy. Thus, to ensure a comfortable fit providing an adequate seal, it is important that the patient interface device fit a patient's face properly to provide an effective seal and that it is comfortable to the patient.

A variety of different types or styles of patient interface devices are known. For example, the SIMPLICITY™ mask and the COMFORTSELECT™ mask, both of which are manufactured Respironics, Inc. of Murrysville, Pa., represent two different types, styles, or families of nasal masks. In addition, a variety of different sizes of masks, such as "small", "medium" and "large", or "adult" and "child", are available with each different mask style. For example, the SIMPLICITY mask is available in two sizes: medium and small; and the COMFORTSELECT mask is available in three sizes: small, medium, and small/wide. Of course there are other styles of masks having other sizes provided by this company and others.

In some patient interface devices, the mask is formed from two components, a mask frame and a cushion that attaches to the frame. The cushion provides the seal against the patient's skin. In these types of patient interface devices, it is known to provide one commonly sized mask frame that can accommodate different sizes and shapes of cushions, thereby effectively providing differently masks within a common mask family. Furthermore, accessories used with the mask, such as the headgear that attach the mask to the user, may have different styles and sizes.

Therefore, to properly fit a patient interface device on a user, the type or style of patient interface device that is best suited for that use must be determined. Then, the appropriate size for that style of patient interface device that best fits the patient must be determined. In addition, in some situations, the appropriate styles and size of accessories, such as headgear and exhalation port, must be determined.

In attempting to determine the proper style of patient interface device that is best suited to a particular patient, the conventional technique has been to have a patient physically try on different styles of masks and allow the patient to select the one they prefer. It can be expected that a style that the patient prefers, may not provide the optimal physical match between the structure of the patient interface device and the anatomical facial features of the patient. For example, a patient may select a style that is aesthetically pleasing over a patient interface device that is less visually appealing but a better fit. In addition, if the patient interface style does not suit the patient, the mask must be cleaned and disinfected prior to use on the next patient, or it should be disposed. Disposing of unused product is obviously wasteful and not profitable. Cleaning and/or disinfecting product is time consuming and may require special equipment or chemicals to properly clean the product.

It is also common for a caregiver to use their best guess or judgment as to which patient interface style will be best suited to the particular facial features of a patient. Of course, this technique relies heavily on the skill and knowledge of the caregiver in knowing the different styles of patient interface devices and the facial features that each style best matches.

Once a style of mask is selected, traditionally the manufacturer of the various types of respiratory masks supplies a sizing gage, also referred to as a template, associated with each type of mask for use in determining which size of that mask is best suited for each user. The sizing template is typically formed from a rigid material with a plurality of cutouts, each cutout corresponding to a different size of the mask. The user places the template on the part of the body to be measured, such as over the nose and/or mouth, to determine which size mask best fits their anatomical features. The user can test their anatomical features in each different size cutout to determine which cutout, and, hence, which size mask, best matches their features.

This template must be available to the provider each time a patient is sized. A disadvantage to this system is the provider must remember to take a sizing gage with them to a patient's residence, in the case of a homecare application, or to the patient's bedside, in the case of a hospital application. It should be apparent that one disadvantage is that this rigid gage may not always be available.

In another sizing technique, "eyeballing" is used. In this instance, the provider will guess the appropriate size product for the patient. It should be apparent that this method can easily result in the selection of the wrong product size. In another sizing procedure, the mask packaging is opened and the product is tried on the patient. As noted above, if the mask is not the correct size, the mask must be cleaned and disinfected prior to use on the next patient, or the mask may be disposed. Of course, disposing of unused product is obviously wasteful and not profitable, and cleaning and/or disinfecting is time consuming and may require special equipment or chemicals.

SUMMARY OF THE INVENTION

Accordingly, it is an object of the present invention to provide technique for selecting a patient interface device or a component thereof from a plurality of known patient interface devices or components that overcomes the shortcomings of conventional selection techniques. This object is achieved according to one embodiment of the present invention by providing a patient interface device selection system that includes a database storing a plurality of sets of data. Each set of data in the plurality of sets of data is associated with a unique patient interface device or a component thereof. A patient data collection system, such as a measuring device or other input device, acquires a set of patient data that correspond to a characteristic of a patient. For example, the patient data can include data corresponding to a dimension of an anatomical feature of such a patient and/or non-anatomically related data (such as whether the patient wears glasses, is claustrophobic, does not like the nostrils to be touched, is sensitive to pressure on the sinuses, was unsuccessful using a particular patient interface device, etc.). A processing system compares the acquired patient data with the plurality of sets of data, and determines the patient interface device or the component thereof that is suitable for use by such a patient based on a result of the comparison. It can thus be appreciated that this patient interface selecting system minimizes product waste, guesswork, and maximizes efficiency in the mask fitting process.

It is yet another object of the present invention to provide a method of selecting a patient interface device for a patient that does not suffer from the disadvantages associated with conventional patient interface device selection techniques. This object is achieved by providing a method that includes storing, on a database, a plurality of sets of data, wherein each set of data in the plurality of sets of data is associated with a unique patient interface device or a component thereof. A set of patient data corresponding to a characteristic of a patient is acquired. The patient data can include, for example, data corresponding to a dimension of an anatomical feature of such a patient, non-anatomically related data, or both. The acquired patient data is compared with the plurality of sets of data to determine the patient interface device or the component thereof suitable for use by such a patient.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
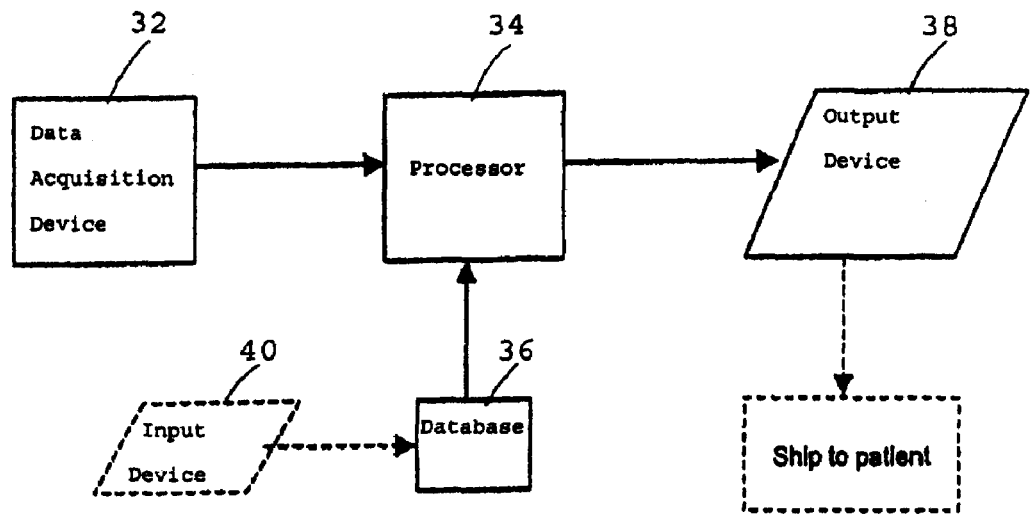
FIG. 1 is a schematic diagram of system for selecting a patient interface device or a component of a patient interface device from a plurality of known patient interface devices or components according to the principles of the present invention.

FIG. 1 schematically illustrates an exemplary embodiment of a system 30 for selecting a patient interface device, or a component of a patient interface device, from a plurality of known patient interface devices or components according to the principles of the present invention according. In its most basic form, system 30 includes a patient data acquisition device 32 that is used to collect patient data associated with at least one characteristic of a patient, a processor 34, a database 36, and an output device 38. As used herein, the term "database" refers to any compilation of information without regard to the format of such information, whether it is stored electronically, via a hardcopy, or in any other way. Thus, "database" is any set of data, and is not limited to data stored on a computer. However, in a presently preferred embodiment, the database is an electronic database stored on a computer.

The present invention contemplates that processor 34 and database 36 are combined as a common processing system. Of course, the database and the processor need not be integrated on a common operating system, and need not be located at a common location. For example, database 36 can reside on one or more storage devices located at virtually any location, e.g., at a patient interface device manufacturer, so long as it can be accessed by the processing system. Likewise, the data acquisition device and output device can be located at the same location as the rest of the system, or each can be located at separate locations. In short, each element of system 30 can be located at separate locations or located at the same site as any other element of the system. A conventional communication link, such as a modem, internet, LAN, WAN, or wireless communication link allows communication between the system components.

System 30 also preferably includes an input device 40 for updating database 36. The present invention contemplates that input device 40 can be any conventional device capable of performing this function, such as a keyboard or keypad. In addition, input device 40 can be a storage medium or communication link that allows for updating the database. For example, the present invention contemplates that input device 36 is a conventional computer terminal that communicates with database using any conventional technique.

Data acquisition device 32 is any device that is capable of providing information concerning a characteristic of a patient, i.e., patient data, to processor 34. For example, one embodiment of the present invention contemplates that the patient data corresponds to a dimension of an anatomical feature the patient. In which case, the data acquisition device is any device that is capable of measuring a distance between landmarks on a patient's face. This distance corresponds to the patient data that is used by processor 34 as discussed below. In its most simplest form, data acquisition device 32 in this embodiment is a measuring instrument, such as a caliper, strait edge with graduated markings, a sizing template, or ruler, that is used to measure a distance between landmarks on such a patient's face. In this embodiment, the manually measured distance or set of distances are manually input to processor 34 as the patient data. For example, common anthropometric landmarks that can be measured and entered as the patient data include, but are not limited to, the nose width (referred to as the alar width), the nose height (referred to as the subnasal-sellion distance), and the head circumference. The present invention contemplates that landmark identifiers or other markings may be placed on the patient to assist in measuring the physical features of the patient directly.

The present invention also contemplates providing a more automated system as data acquisition device 32 for measuring an anatomical feature of the patient. For example, devices are known that are capable of generating a three-dimensional representation of at least a portion of such a patient's face. Examples of such devices include optical scanners, cameras, and push-pin arrays. The patient data is derived from the three-dimensional image using any conventional technique. For example, a patient needing a patient interface device may have his or her face scanned at a scanning station located at a first location, such as a sleep lab or hospital. The image information can be sent to a second location, such as a patient interface device manufacturer. It is at this location that the patient data, i.e., the distance or size information needed to determine which style and size of patient interface device or component thereof that is suited for that patient, is determined and then provided to processor 34.

In another embodiment of the present invention, the patient data corresponds to information gathered from the patient that is not related to a dimension of an anatomical feature the patient. In which case, data acquisition device 32 is any device that is capable of collecting this information. For example, the present invention contemplates that the patient data can include information about patient or the patient's "lifestyle". For example, knowing whether the patient wears glasses or is claustrophobic is helpful in selecting a suitable patient interface device. Examples of this "lifestyle" related information that can be collected as the patient data include information concerning the following:

- gender, race, age, or geographic location of the patient,
- whether the patient wears glasses or a hearing aid,
- the patient's pressure support prescription (pressure level, mode of pressure support);
- whether the patient is receiving supplemental oxygen;
- whether the patient is claustrophobic;
- whether the patient has allergies or other medical conditions,
- whether the patient breathes through his or her mouth during sleep,
- whether the patient does not like the nostrils to be touched,
- whether the patient is sensitive to pressure on the sinuses,
- whether humidification is to be used with the pressure support therapy, and
- what other patient interface device may have been used by the patient and the success of such devices.

The purpose of this last item is to prevent the system from suggesting a patient interface device or component if the patient has already rejected that device or component. It should be readily apparent that this list of patient data is not complete or exhaustive.

The present invention contemplates that the data acquisition device that is used to collect this "lifestyle" type of patient data can be any device capable of performing this function, such as computer terminal, PDA device, such as a PALM handheld device, telephone survey, or manual questionnaire. Again, the function of the data acquisition device is to provide this information to the processor for comparison to stored information, as discussed in detail below. Therefore, any hardware or technique that is capable of collecting this information and providing it to the processor is suitable for use in the present invention.

As noted above, the patient data is preferably stored in a database. However, the present invention also contemplates that the patient data can be stored on a portable medium so that the patient or the patient's caregiver can keep a record of their patient data. Although this information can be updated as needed, providing the patient data on this portable medium, such as a smartcard, CD-ROM, or disk, avoids the need to recollect the patient data each time the patient wants to try or is prescribed a different patient interface device or treatment.

Processor 34 compares the patient data with a plurality of sets of data, which is stored in the database. One end result of this comparison is to identify a patient interface device, by style, size, or both, from those stored in the database, that is suitable for use by such a patient. More specifically, the preferable end result is to identify the patient interface device by style, size, or both, or to identify alternative patient interface devices that represent a best fit in terms of comfort and effectiveness for that particular patient from among all of the available patient interface device styles and sizes stored on the database. The output of this comparison is provided by output device 36. If the patient interface device manufacturer performs the comparison, this output information may be used to ship the selected patient interface device to the patient or caregiver responsible for supervising the patient. If the caregiver or some party other than the manufacturer performs this comparison, the output data is typically used to select the patient interface device or component from an existing inventory or to order it from the device manufacturer or other distributor.

The present invention also contemplates using the processor to determine more than just the appropriate patient interface device for a patient based on the input patient data. The patient data can also be used to configure the selected patient interface device. It is known that a patient interface device or component may have one or more adjustable features. For example, it is known to provide a forehead support on a nasal or nasal/oral mask, where the forehead support is capable of being located in a plurality of discrete locations. It is also known to provide a similar adjustability for the headgear that attaches a mask to the patient. The present invention contemplates using the patient data to determine a starting position for the adjustable features of the patient interface device or component, such as a suggested starting position for the forehead support or the headgear strap based on the patient data. For example, the present invention contemplates storing, for each patient interface device or component, a table of settings for each adjustable feature of that patient interface device or component, and selecting the appropriate setting for that device or component based on the input patient data.

Figure 2A:
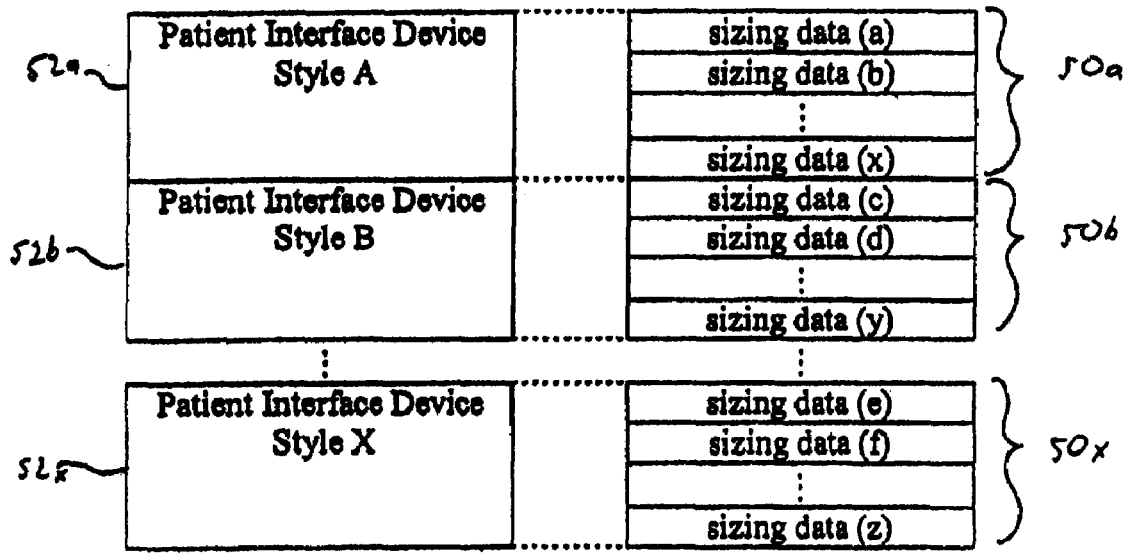
FIGS. 2A-2C illustrate exemplary embodiments of databases suitable for use in the system of FIG. 1.
Figure 2B:
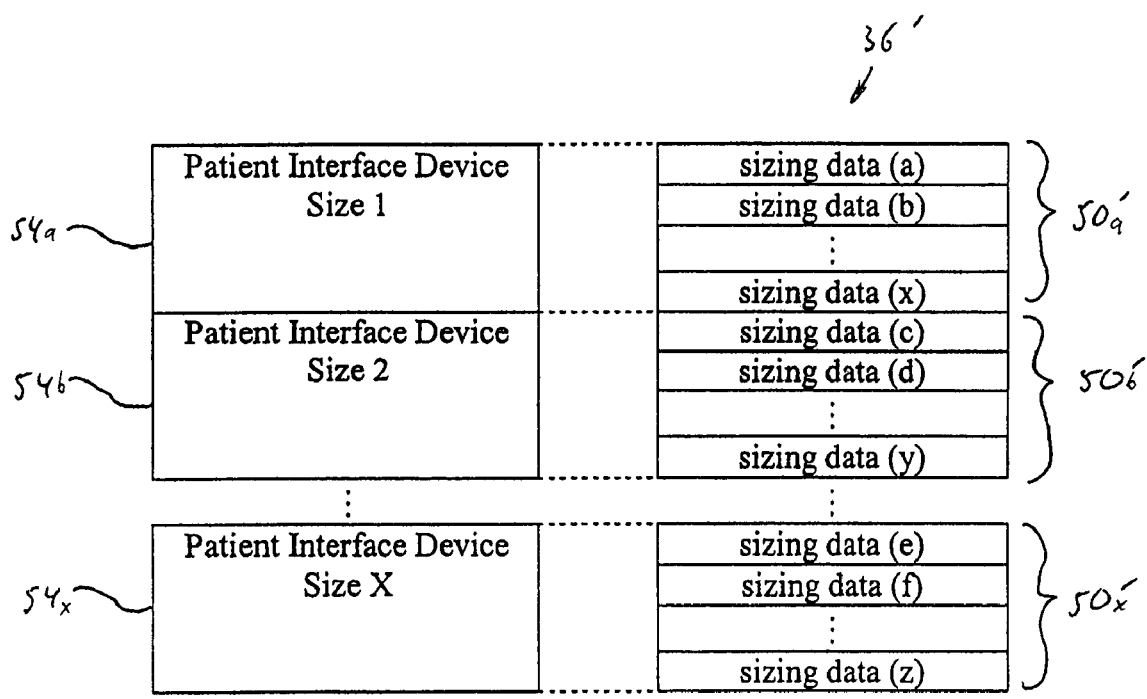
Figure 2C:
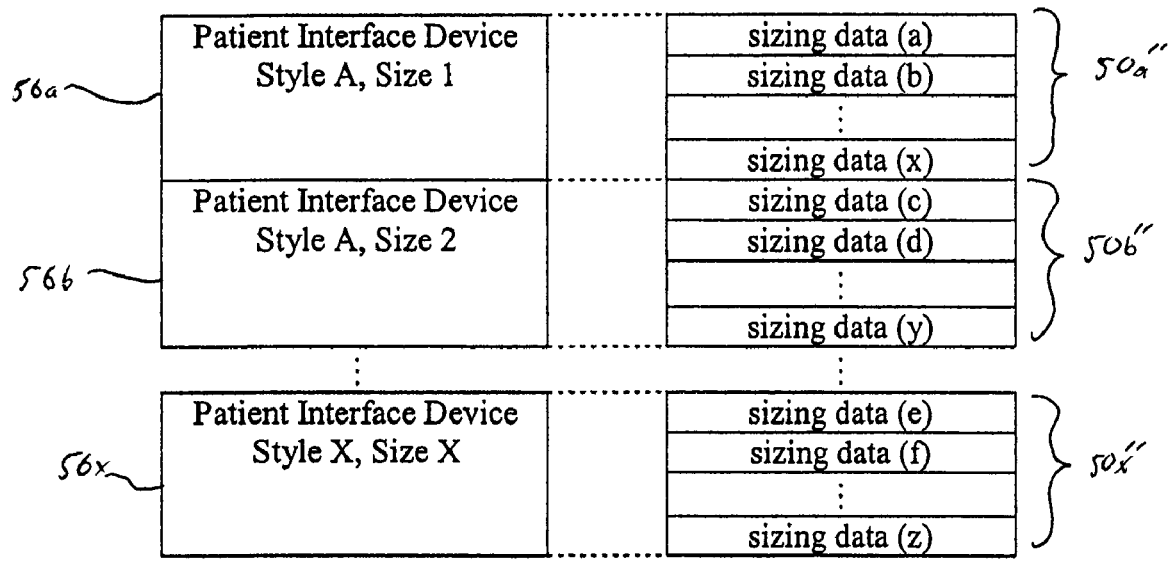

FIGS. 2A-2C illustrate exemplary embodiment of database 36, 36', 36" for use in the system of the present invention. FIG. 2A illustrates a database 36 in which a unique set of data 50*a*, 50*b*, . . . 50*x* is associated with each style of patient interface device 52*a*, 52*b*, . . . 52*x* stored therein. In this system, the processor compares the input patient data with the different sets of stored data to determine which style of patient interface device 52*a*, 52*b*, . . . 52*x* is best suited for that patient. Each set of data 50*a*, 50*b*, . . . 50*x* can have as few as one piece of data or each set can have multiple pieces of data associated therewith. This database is particularly suited for situations where each style of patient interface device has only one size, so that no size selection within each style is needed.

FIG. 2B illustrates a database 36' in which a unique set of data 50*a'*, 50*b'*, . . . 50*x'* is associated with each size of patient interface device 54 stored therein. In this system, the processor compares the input patient data with the different sets of stored data $50a', 50b', \ldots 50x'$ to determine which size of patient interface device $54a, 54b, \ldots 54x$ is best suited for that patient. As noted above, each set of data can have as few as one piece of data or each set can have multiple pieces of data associated therewith. This database is particularly suited for situations where there is only one style of patient interface device, so that the selection of the appropriate patient interface device for that patient is based only on size.

Finally, FIG. 2C illustrates a database 36" in which a unique set of data $50a'', 50b', \ldots 50x''$ is associated with each style and size of patient interface device 56 stored therein. In this system, the processor compares the input patient data with the different sets of stored data to determine which style and size of patient interface device $56a, 56b, \ldots 56x$ is best suited for that patient. Again, each set of data $50a', 50b'', \ldots 50x''$ can have as few as one piece of data or each set can have multiple pieces of data associated therewith. This database is particularly suited for situations where there are multiple styles of patient interface devices and for at least one style there is more than one size, so that selecting the optimal patient interface device requires selecting the appropriate style and size using the patient interface data. Of course, the sets of data associated with a common style of patient interface device may have similar types of data associated therewith.

As alluded to above, the present invention contemplates that the processor identifies more than one patient interface device style and/or size that is suitable for the patient. For example, it may be the case that a small size patient interface device in a first style and a large size patient interface device in a second style may provide nearly the same optimal match with the patient data. This would allow that patient or caregiver to have further flexibility in finally selecting which patient interface device to use.

In addition, the present invention contemplates that in situations where multiple patient interface devices are selected as being suitable for use by a patient, the processor rank the plurality of patient interface devices based on a degree of match between the patient data and the plurality of sets of data associated with the plurality of patient interface devices. This allows the patient or caregiver to have further information as to which patient interface device from the plurality of devices is more likely to be best suited for that patient.

In a further embodiment of the present invention, system 30 includes the capability of storing the patient data in a database, which can be database 36 or a separate patient data database. Of course, this information can be stored in any conventional manner. One advantage of maintaining the patient data in a database is to allow this information to be compared with any new data that may be added to database 36. For example, a patient interface device manufacturer may develop a new style of patient interface device, perhaps having several sizes, or may develop a new size of an existing style. The processor can be used to compare the stored patient data and the new set of data to determine if the new patient interface device is better suited for use by the patient than the previously selected patient interface device.

In the embodiment discussed above, the primary focus was on selecting a patient interface device for a patient. However, as noted above, a patient interface device can have multiple components, where one of these components may have multiple styles and/or sizes. For example, it is known that a nasal mask can include a mask shell and a cushion that removeably attaches to the shell. The cushion can be provided in different sizes and shapes, i.e., styles, so that each different mask and cushion combination is, in effect, a unique patient interface device. To account for this, the present invention contemplates treating each different combination as a unique patient interface device and storing a set of sizing information based on each unique patient interface device. On the other hand, the present invention contemplates storing a set of data associated with the component of the patient interface device, such as the data corresponding to different styles of cushions that can attach to a common mask shell or frame, so that the appropriate component can be selected based on the stored data and the input patient data. This technique can be used to select any desired component of the a patient interface device, such as a headgear, cushion, frame, or patient circuit.

In the embodiments discussed above, it was assumed that the patient interface device or component was a finished product. In other words, the patient interface device or component was suitable for use by the patient as is, i.e., without further modification of the device or component, other than perhaps adjusting an adjustable feature of the patient interface device or component. A further embodiment of the present invention, however, contemplates that the patient interface device or component need not be a completely finished product, but may be finished based on the patient data.

According to this embodiment of the present invention, one or more different templates for the patient interface device or component of the device are provided. For example, the seal or cushion used on a nasal mask may be used as the template. This template must be capable of being modified in some manner. For example, the shape of the patient contacting portion of the seal must be capable of being modified. Such modifiable seals are known. See, e.g., U.S. Pat. No. 6,397,847. The template is then modified based on the patient data. If necessary, the modified component or components are joined to form the patient interface device. The database can store information concerning the templates that are modified, so that the appropriate template can be selected from the patient data and then further modified based on that same data.

A still further embodiment of the present invention contemplates providing a patient interface customization option. This options provides a "catch-all" or "other" option if, for example, the comparison of the patient data with the data stored in the database does not produce a suitable match. Suppose, for example, that the patient data for a particular patient is collected and entered into the system for comparison to the sets of data stored in the database. If, as a result of that comparison, no suitable match is made between the patient data and the plurality of sets of data stored in the database, the system can suggest a "customization" option for the patient interface device best suited for that patient. If this option is selected, the system uses the collected patient data to fabricate a customized mask using any customization technique, i.e., from scratch or by modifying a template—that is preferably selected from among the possible templates as discussed above. This embodiment allows the system to provide a suggestion as the type of patient interface device for any patient. The present invention also contemplates that this customization option can be manually selected by the user, if desired, so that the customized mask can be fabricated and provided to the patient even if a suitable patient interface device for that patient is otherwise available from the patient interface devices stored in the database.

It can thus be appreciated that the present invention provides an automated technique for using patient data collecting using any conventional technique to determine which patient interface device is best suited for that patient. This is accomplished without having the patient try on, and thus contaminate, several patient interface device, and without relying on the experience or guesswork of a caregiver to select the right patient interface device for a particular patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method of selecting a patient interface device or at least one component thereof comprising:
   storing, on a database, a plurality of sets of data, wherein each set of data in the plurality of sets of data is associated with a unique patient interface device, and wherein the patient interface device is a device adapted to communicate a flow of gas to an airway of a patient;
   acquiring patient data corresponding to at least one characteristic of a patient, wherein the patient data includes anatomical data indicative of a dimension of an anatomical feature of such a patient associated with at least a portion of a head of such a patient;
   comparing the patient data with the plurality of sets of data; and
   determining the patient interface device suitable for use by such a patient based on a result of the comparing of the patient data with the plurality of sets of data.

2. The method of claim 1, wherein each of the plurality of sets of data comprises data associated with a physical dimension of the unique patient interface device associated with that respective set of data.

3. The method of claim 1, wherein each of the plurality of sets of data comprises data not associated with a physical dimension of the unique patient interface device associated with that respective set of data, and wherein the patient data further comprises data that does not correspond to a dimension of an anatomical feature of such a patient.

4. The method of claim 1, wherein determining the patient interface device includes determining a style of the patient interface device from a plurality of different styles of patient interface devices.

5. The method of claim 1, wherein determining the patient interface device includes determining a size of the patient interface device from a plurality of differently sized patient interface devices.

6. The method of claim 1, wherein determining the patient interface device includes: (1) determining a style of patient interface device from a plurality of different styles of patient interface devices, and (2) determining a size of patient interface device from a plurality of differently sized patient interface devices associated with the determined style of patient interface device.

7. The method of claim 1, wherein acquiring the set of patient data includes measuring a distance between landmarks on such a patient's face, wherein the patient data includes the measured distance.

8. The method of claim 1, wherein acquiring the set of patient data includes generating a three-dimensional representation of at least a portion of such a patient's face.

9. The method of claim 1, wherein acquiring a set of patient data is done at a first location, further comprising transmitting the patient data to a second location for performing the comparing.

10. The method of claim 1, wherein determining the patient interface device suitable for use by such a patient includes determining a plurality of patient interface devices that are suitable for use by such a patient.

11. The method of claim 10, further comprising ranking the patient interface devices in the plurality of patient interface devices based on a degree of match between the patient data and the plurality of sets of data.

12. The method of claim 1, wherein the patient interface device includes an adjustable feature, and further comprising: determining a setting, based on the patient data, for the adjustable feature of the patient interface device determined in the patient interface determining step.

13. The method of claim 1, further comprising storing the patient data in the database.

14. The method of claim 13, further comprising:
   entering into the database a new set of data corresponding to a new patient interface device; and
   repeating the comparing and the determining step using the stored patient data and the plurality of sets of data including the new set of data.

15. A system for selecting a patient interface device for a patient comprising:
   a database storing a plurality of sets of data, wherein each set of data in the plurality of sets of data is associated with a unique patient interface device, and wherein the patient interface device is a device adapted to communicate a flow of gas to an airway of a patient;
   means for acquiring a set of patient data corresponding to at least one characteristic of a patient, wherein the patient data includes anatomical data indicative of a dimension of an anatomical feature of such a patient associated with at least a portion of a head of such a patient; and processing means for comparing the patient data with the plurality of sets of data, and for determining the patient interface device suitable for use by such a patient based on a result of the comparison.

16. The system of claim 15, wherein each of the plurality of sets of data comprises data associated with a physical dimension of the unique patient interface device associated with that respective set of data.

17. The system of claim 15, wherein each of the plurality of sets of data comprises data not associated with a physical dimension of the unique patient interface device associated with that respective set of data, and wherein the patient data further comprises data that does not correspond to a dimension of an anatomical feature of such a patient.

18. The system of claim 15, wherein the processing means determines a style of the patient interface device from a plurality of different styles of patient interface devices.

19. The system of claim 15, wherein the processing means determines a size of the patient interface device from a plurality of differently sized patient interface devices.

20. The system of claim 15, wherein the processing means determines: (1) a style of patient interface device from a plurality of different styles of patient interface devices, and (2) a size of patient interface device from a plurality of differently sized patient interface devices associated with the determined style of patient interface device.

21. The system of claim 15, wherein the means for acquiring the set of patient data is a measuring instrument adapted to measure a distance between landmarks on such a patient's face, wherein the patient data includes the measured distance.

22. The system of claim 15, wherein the means for acquiring the set of patient data includes means for generating a three-dimensional representation of at least a portion of such a patient's face.

23. The system of claim 15, wherein the means for acquiring a set of patient data is located at a first location, and further comprising means for transmitting the patient data to a second location.

24. The system of claim 15, wherein the processing means determines a plurality of patient interface devices that are suitable for use by such a patient.

25. The system of claim 24, wherein the processing means ranks the plurality of patient interface devices based on a degree of match between the patient data and the plurality of sets of data.

26. The system of claim 15, wherein the patient interface device includes an adjustable feature, and wherein the processing means determines a setting, based on the patient data, for the adjustable feature of the patient interface device determined to be suitable for such a patient.

27. The system of claim 15, further comprising means for storing the patient data in the database.

28. The system of claim 27, further comprising means for entering into the database a new set of data corresponding to a new patient interface device, and wherein the processing means compares the stored patient data and the plurality of sets of data including the new set of data to determine the patient interface device suitable for use by such a patient based on a result of the comparison.

29. A method of selecting a patient interface device or at least one component thereof for a patient comprising:
   storing, on a database, a plurality of sets of data, wherein each set of data in the plurality of sets of data is associated with a unique component of a patient interface device, and wherein the patient interface device is a device adapted to communicate a flow of gas to an airway of a patient;
   acquiring patient data corresponding to at least one characteristic of a patient, wherein the patient data includes anatomical data indicative of a dimension of an anatomical feature of such a patient associated with at least a portion of a head of such a patient;
   comparing the patient data with the plurality of sets of data; and
   determining the component of the patient interface device suitable for use by such a patient based on a result of the comparing of the patient data with the plurality of sets of data.

30. The method of claim 29, wherein each of the plurality of sets of data comprises data associated with a physical dimension of the unique component of the patient interface device associated with that respective set of data.

31. The method of claim 29, wherein each of the plurality of sets of data comprises data not associated with a physical dimension of the unique component of the patient interface device associated with that respective set of data, and wherein the patient data further comprises data that does correspond to a dimension of an anatomical feature of such a patient.

32. The method of claim 29, wherein determining the component of the patient interface device includes determining a style of the patient interface device or the component from a plurality of different styles of patient interface devices or components.

33. The method of claim 29, wherein determining the component of the patient interface device includes determining a size of the component from a plurality of differently sized components.

34. The method of claim 29, wherein determining the component of the patient interface device includes: (1) determining a style of the component of the patient interface device from a plurality of different styles of components, and (2) determining a size of the component from a plurality of differently sized components associated with the determined style of component.

35. The method of claim 29, wherein acquiring the set of patient data includes measuring a distance between landmarks on such a patient's face, wherein the patient data includes the measured distance.

36. The method of claim 29, wherein acquiring the set of patient data includes generating a three-dimensional representation of at least a portion of such a patient's face.

37. The method of claim 29, wherein acquiring a set of patient data is done at a first location, further comprising transmitting the patient data to a second location for performing the comparing.

38. The method of claim 29, wherein determining the component of the patient interface device suitable for use by such a patient includes determining a plurality of components of patient interface devices that are suitable for use by such a patient.

39. The method of claim 38, further comprising ranking the components of the patient interface devices in the plurality of components based on a degree of match between the patient data and the plurality of sets of data.

40. The method of claim 29, wherein the component of the patient interface device includes an adjustable feature, and further comprising: determining a setting, based on the patient data, for the adjustable feature of the component of the patient interface device determined in the patient interface determining step.

41. The method of claim 29, further comprising storing the patient data in the database.

42. The method of claim 41, further comprising:
   entering into the database a new set of data corresponding to a new component of a patient interface device; and
   repeating the comparing and the determining step using the stored patient data and the plurality of sets of data including the new set of data.

43. A system for selecting a patient interface device for a patient comprising:
   a database storing a plurality of sets of data, wherein each set of data in the plurality of sets of data is associated with a unique component of a patient interface device, and wherein the patient interface device is a device adapted to communicate a flow of gas to an airway of a patient;
   means for acquiring a set of patient data corresponding to at least one characteristic of a patient, wherein the patient data includes anatomical data indicative of a dimension of an anatomical feature of such a patient associated with at least a portion of a head of such a patient; and
   processing means for comparing the patient data with the plurality of sets of data, and for determining the component of the patient interface device suitable for use by such a patient based on a result of the comparison.

44. The system of claim 43, wherein each of the plurality of sets of data comprises data associated with a physical dimension of the unique component of the patient interface device associated with that respective set of data.

45. The system of claim 43, wherein each of the plurality of sets of data comprises data not associated with a physical dimension of the unique component of the patient interface device associated with that respective set of data, and wherein the patient data further comprises data that does not correspond to a dimension of an anatomical feature of such a patient.

46. The system of claim 43, wherein the processing means determines a style of the component of the patient interface device from a plurality of different styles of components.

47. The system of claim 43, wherein the processing means determines a size of the component of the patient interface device from a plurality of differently sized components.

48. The system of claim 43, wherein the processing means determines: (1) a style of component of the patient interface device from a plurality of different styles of components, and (2) a size of the component of the patient interface device from a plurality of differently sized components associated with the determined style of component.

49. The system of claim 43, wherein the means for acquiring the set of patient data is a measuring instrument adapted to measure a distance between landmarks on such a patient's face, wherein the patient data includes the measured distance.

50. The system of claim 43, wherein the means for acquiring the set of patient data includes means for generating a three-dimensional representation of at least a portion of such a patient's face.

51. The system of claim 43, wherein the means for acquiring a set of patient data is located at a first location, and further comprising means for transmitting the patient data to a second location.

52. The system of claim 43, wherein the processing means determines a plurality of components of patient interface devices that are suitable for use by such a patient.

53. The system of claim 52, wherein the processing means ranks the plurality of components of patient interface devices based on a degree of match between the patient data and the plurality of sets of data.

54. The system of claim 43, further comprising means for storing the patient data in the database.

55. The system of claim 54, farther comprising means for entering into the database a new set of data corresponding to a new component of a patient interface device, and wherein the processing means compares the stored patient data and the plurality of sets of data including the new set of data to determine the component of the patient interface device suitable for use by such a patient based on a result of the comparison.

56. The system of claim 43, wherein the component of the patient interface device includes an adjustable feature, and wherein the processing means determines a setting, based on the patient data, for the adjustable feature of the component of the patient interface device determined to be suitable for such a patient.

* * * * *